United States Patent
Thompson

(10) Patent No.: US 12,281,309 B1
(45) Date of Patent: Apr. 22, 2025

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/889,137

(22) Filed: Sep. 18, 2024

(51) Int. Cl.
*C12N 15/113* (2010.01)
*C12N 15/86* (2006.01)

(52) U.S. Cl.
CPC .......... *C12N 15/1137* (2013.01); *C12N 15/86* (2013.01); *C12N 2310/141* (2013.01); *C12N 2750/14143* (2013.01)

(58) Field of Classification Search
CPC ................ C12N 15/1137; C12N 15/86; C12N 2310/141; C12N 2750/14143
See application file for complete search history.

(56) References Cited

PUBLICATIONS

O'Brien et al. "Overview of MicroRNA Biogenesis, Mechanisms of Actions, and Circulation," Frontiers in Endocrinology, vol. 9, Article 402: 1-12 (2018). (Year: 2018).*

Zhang et al. "The Risks of miRNA Therapeutics: In a Drug Target Perspective," Drug Design, Development and Therapy 15: 721-733 (2021). (Year: 2021).*
Ha et al. "Interspecies Regulation of MicroRNAs and Their Targets," Biochim Biophys Acta. 1779(11): 735-742 (2008). (Year: 2008).*
Taylor & Kornev "Protein kinases: evolution of dynamic regulatory proteins," Trends in Biochemical Sciences, vol. 36, Issue 2, 65-77 (2011). (Year: 2011).*
Scheef & Bourne. "Structural evolution of the protein kinase-like superfamily," PLoS Comput Biol. Oct. 2005;1(5):e49. (Year: 2005).*
Ramaiah et al. "miR-15/16 complex targets p70S6 kinase1 and controls cell proliferation in MDA-MB-231 breast cancer cells," Gene, vol. 552, Issue 2, Dec. 1, 2014, pp. 255-264. (Year: 2014).*

* cited by examiner

*Primary Examiner* — Richard A Schnizer
*Assistant Examiner* — Amanda M Zahorik
(74) *Attorney, Agent, or Firm* — Gowling WLG (Canada) LLP

(57) ABSTRACT

The embodiments of the present disclosure relate to one or more compositions or methods that upregulate the production of one or more sequences of micro-interfering ribonucleic acid (miRNA). The sequences of miRNA may be complimentary to a sequence of target messenger RNA (mRNA) that encodes for translation of a target biomolecule, such as JAK. The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to expression of the target biomolecule.

6 Claims, No Drawings
Specification includes a Sequence Listing.

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "A8149790US-SequenceListing.xml" created on 2024 Sep. 12 and having a size of 15,902 bytes. The information contained in the Sequence Listing is incorporated by reference herein.

TECHNICAL FIELD

The present disclosure generally relates to compositions for regulating production of micro-interfering ribonucleic acid (miRNA). In particular, the present disclosure relates to compositions for regulating gene expression and therefore, the production of miRNA that will suppress Janus kinase (JAK) expression.

BACKGROUND

Bioactive molecules, including receptors, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in bioavailability of the target biomolecule within a subject that is administered the one or more compositions. In some embodiments of the present disclosure, the target biomolecule is a kinase molecule such as Janus kinase (JAK).

In some embodiments of the present disclosure the compositions comprise a plasmid of deoxyribonucleic acid (DNA) that includes one or more insert sequences of nucleotides that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a composition that comprises a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of JAK.

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example JAK. A first approach utilizes gene vectors containing nucleotide sequences for increasing the endogenous production of one or more sequences of miRNA, which are complete or partial sequences and/or combinations thereof, that target and silence the mRNA of JAK, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject, such as Janus kinase (JAK). A biomolecule may be endogenous or exogenous to a subject and when bioavailable the biomolecule may supress, influence or stimulate a physiological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.c., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production and/or activation of one or more target biomolecules. The miRNA may, directly or indirectly, bind to and degrade the mRNA of the target biomolecule, also referred to as the target mRNA, or otherwise inactivate the target mRNA so that less or none of the target-biomolecule protein is produced.

In some embodiments of the present disclosure, the target biomolecule is JAK.

In some embodiments of the present disclosure, the insert comprises one or more nucleotide sequences that each encode one or more miRNA sequences that may be complimentary to and degrade, or cause degradation and/or inactivation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as JAK. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as JAK.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass. In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with an example being JAK. The RP is comprised of AAV2 inverted terminal repeats (ITRs), a composite CASI promoter, a human growth hormone (HGH) signal peptide followed by a miRNA expression cassette containing up to six different miRNAs targeting the mRNA of JAK, followed by a Woodchuck Hepatitis Virus post-transcriptional regulatory element (WPRE) and an SV40 polyA signal.

```
SEQ ID NO. 1 (backbone sequence No. 1):
5'
TCTAGAATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGC
TATTGCTTCCCGTATGGCTTTCATTTTCTCCTCCTTGTATAAATCCTGGTTGCTGTCTC
TTTATGAGGAGTTGTGGCCCGTTGTCAGGCAACGTGGCGTGGTGTGCACTGTGTTTG
CTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCG
CTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACG
TCCTTCTGCTACGTCCCTTCGGCCCTCAATCCAGCGGACCTTCCTTCCCGCGGCCTGC
TGCCGGCTCTGCGGCCTCTTCCGCGTCTTCGCCTTCGCCCTCAGACGAGTCGGATCTC
CCTTTGGGCCGCCTCCCCGCCTAAGCTTATCGATACCGTCGAGATCTAACTTGTTTAT
TGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
GTCTGGATCTGACCTCGACTAGAGCATGGCTACGTAGATAAGTAGCATGCGGGTT
AATCATTAACTACAAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCC
GGGCGGCCTCAGTGAGCGAGCGAGCGCGCAGCTGGCGTAATAGCGAAGAGGCCCG
CACCGATCGCCCTTCCCAACAGTTGCGCAGCCTGAATGGCGAATGGCGATTCCGTTG
CAATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGTTA
ATTTGCGTGATGGACAGACTCTTTTACTCGGTGGCCTCACTGATTATAAAAACACTT
CTCAGGATTCTGGCGTACCGTTCCTGTCTAAAATCCCTTTAATCGGCCTCCTGTTTAG
CTCCCGCTCTGATTCTAACGAGGAAAGCACGTTATACGTGCTCGTCAAAGCAACCAT
AGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGG
TTCACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCTCG
GTCTATTCTTTTGATTTATAAGGGATTTTGCCGATTTCGGCCTATTGGTTAAAAAATG
AGCTGATTTAACAAAAATTTAACGCGAATTTTAACAAAATATTAACGTTTACAATTT
AAATATTTGCTTATACAATCTTCCTGTTTTTGGGGCTTTTCTGATTATCAACCGGGGT
ACATATGATTGACATGCTAGTTTTACGATTACCGTTCATCGATTCTCTTGTTTGCTCC
AGACTCTCAGGCAATGACCTGATAGCCTTTGTAGAGACCTCTCAAAAATAGCTACCC
TCTCCGGCATGAATTTATCAGCTAGAACGGTTGAATATCATATTGATGGTGATTTGA
CTGTCTCCGGCCTTTCTCACCCGTTTGAATCTTTACCTACACATTACTCAGGCATTGC
ATTTAAAATATATGAGGGTTCTAAAAATTTTTATCCTTGCGTTGAAATAAAGGCTTCT
CCCGCAAAAGTATTACAGGGTCATAATGTTTTTGGTACAACCGATTTAGCTTTATGC
```

-continued

```
TCTGAGGCTTTATTGCTTAATTTTGCTAATTCTTTGCCTTGCCTGTATGATTTATTGGA
TGTTGGAATTCCTGATGCGGTATTTTCTCCTTACGCATCTGTGCGGTATTTCACACCG
CATATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTTCACCGTC
ATCACCGAAACGCGCGAGACGAAAGGGCCTCGTGATACGCCTATTTTTATAGGTTAA
TGTCATGATAATAATGGTTTCTTAGACGTCAGGTGGCACTTTTCGGGGAAATGTGCG
CGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCA
ACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTG
ACAACGATCGGAGGACCGAAGGAGCTAACCGCTTTTTTGCACAACATGGGGGATCA
TGTAACTCGCCTTGATCGTTGGGAACCGGAGCTGAATGAAGCCATACCAAACGACG
AGCGTGACACCACGATGCCTGTAGCAATGGCAACAACGTTGCGCAAACTATTAACT
GGCGAACTACTTACTCTAGCTTCCCGGCAACAATTAATAGACTGGATGGAGGCGGAT
AAAGTTGCAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAAC
TGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGTTAGGCCA
CCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAA
AGCGCCACGCTTCCCGAAGGGAGAAAGGCGGACAGGTATCCGGTAAGCGGCAGGG
TCGGAACAGGAGAGCGCACGAGGGAGCTTCCAGGGGAAACGCCTGGTATCTTTAT
AGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCCTCTCC
CCGCGCGTTGGCCGATTCATTAATGCAGCAGCTGCGCGCTCGCTCGCTCACTGAGGC
CGCCCGGGCAAAGCCCGGGCGTCGGGCGACCTTTGGTCGCCCGGCCTCAGTGAGCG
AGCGAGCGCGCAGAGAGGGAGTGGCCAACTCCATCACTAGGGGTTCCTTGTAGTTA
ATGATTAACCCGCCATGCTACTTATCTACGTAGCCATGCTCTAGGACATTGATTATTG
ACTAGTGGAGTTCCGCGTTACATAACTTACGGTAAATGGCCCGCCTGGCTGACCGCC
CAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTG
CTTCACTCTCCCCATCTCCCCCCCCTCCCCACCCCCAATTTTGTATTTATTTATTTTTT
AATTATTTTGTGCAGCGATGGGGCGGGGGGGGGGGGCGCGCGCCAGGCGGG
GCGGGCGGGGCGAGGGCGGGGCGGGCGAGGCGGAGAGGTGCGGCGGCAGCCA
ATCAGAGCGGCGCGCTCCGAAAGTTTCCTTTTATGGCGAGGCGGCGGCGGCGGCGG
CCCTATAAAAGCGAAGCGCGCGGCGGGCGGGAGTCGCTGCGCGCTGCCTTCGCCC
CGTGCCCCGCTCCGCCGCCGCCTCGCGCCGCCCGCCCCGGCTCTGACTGACCGCGTT
ACTAAAACAGGTAAGTCCGGCCTCCGCGCCGGGTTTTGGCGCCTCCCGCGGGCGCCC
CCCTCCTCACGGCGAGCGCTGCCACGTCAGACGAAGGGCGCAGCGAGCGTCCTGAT
CCTTCCGCCCGGACGCTCAGGACAGCGGCCCGCTGCTCATAAGACTCGGCCTTAGAA
CCCCAGTATCAGCAGAAGGACATTTTAGGACGGGACTTGGGTGACTCTAGGGCACT
GGTTTTCTTTCCAGAGAGCGGAACAGGCGAGGAAAAGTAGTCCCTTCTCGGCGATTC
TGCGGAGGGATCTCCGTGGGGCGGTGAACGCCGATGATGCCTCTACTAACCATGTTC
ATGTTTTCTTTTTTTTTCTACAGGTCCTGGGTGACGAACAGGGTACC
3'

SEQ ID NO. 2 (miRNA expression cassette No. 2 - JAK):
5'
ATGGCCACCGGCTCTCGCACAAGCCTGCTGCTGGCTTTCGGACTGCTGTGCCTGCCT
TGGCTCCAGGAGGGCTCCGCCGCTAGCATCGATACCGTCGCTATGTGCTGGAGGCTT
GCTGAAGGCTGTATGCTGTATCTTCCGGATGTCATAGCGGCGTTTTGGCCTCTGACT
GACGCCGCTATGATCCGGAAGATACAGGACACAAGGCCTGTTACTAGCACTCACAT
GGAACAAATGGCCTCTAGCCTGGAGGCTTGCTGAAGGCTGTATGCTGTATGTTTATG
GATCTCACCTGGCGTTTTGGCCTCTGACTGACGCCAGGTGAGCCATAAACATACAGG
ACACAAGGCCTGTTACTAGCACTCACATGGAACAAATGGCCTCTAGCCTGGAGGCTT
GCTGAAGGCTGTATGCTGTCACTTTCAGAAATCATGGGTGCGTTTTGGCCTCTGACT
GACGCACCCATGATCTGAAAGTGACAGGACACAAGGCCTGTTACTAGCACTCACAT
GGAACAAATGGCCTC
3'
```

-continued

SEQ ID NO: 3 = SEQ ID NO: 1 + SEQ ID NO: 2

5'
TCTAGAATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGC
TATTGCTTCCCGTATGGCTTTCATTTTCTCCTCCTTGTATAAATCCTGGTTGCTGTCTC
TTTATGAGGAGTTGTGGCCCGTTGTCAGGCAACGTGGCGTGGTGTGCACTGTGTTTG
CTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCG
CTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACG
TCCTTCTGCTACGTCCCTTCGGCCCTCAATCCAGCGGACCTTCCTTCCCGCGGCCTGC
TGCCGGCTCTGCGGCCTCTTCCGCGTCTTCGCCTTCGCCCTCAGACGAGTCGGATCTC
CCTTTGGGCCGCCTCCCCGCCTAAGCTTATCGATACCGTCGAGATCTAACTTGTTTAT
TGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
GTCTGGATCTCGACCTCGACTAGAGCATGGCTACGTAGATAAGTAGCATGGCGGGTT
AATCATTAACTACAAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCC
GGGCGGCCTCAGTGAGCGAGCGAGCGCGCAGCTGGCGTAATAGCGAAGAGGCCCG
CACCGATCGCCCTTCCCAACAGTTGCGCAGCCTGAATGGCGAATGGCGATTCCGTTG
CAATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGTTA
ATTTGCGTGATGGACAGACTCTTTTACTCGGTGGCCTCACTGATTATAAAAACACTT
CTCAGGATTCTGGCGTACCGTTCCTGTCTAAAATCCCTTTAATCGGCCTCCTGTTTAG
CTCCCGCTCTGATTCTAACGAGGAAAGCACGTTATACGTGCTCGTCAAAGCAACCAT
AGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGG
TTCACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCTCG
GTCTATTCTTTTGATTTATAAGGGATTTTGCCGATTTCGGCCTATTGGTTAAAAAATG
AGCTGATTTAACAAAAATTTAACGCGAATTTTAACAAAATATTAACGTTTACAATTT
AAATATTTGCTTATACAATCTTCCTGTTTTTGGGGCTTTTCTGATTATCAACCGGGGT
ACATATGATTGACATGCTAGTTTTACGATTACCGTTCATCGATTCTCTTGTTTGCTCC
AGACTCTCAGGCAATGACCTGATAGCCTTTGTAGAGACCTCTCAAAAATAGCTACCC
TCTCCGGCATGAATTTATCAGCTAGAACGGTTGAATATCATATTGATGGTGATTTGA
CTGTCTCCGGCCTTTCTCACCCGTTTGAATCTTTACCTACACATTACTCAGGCATTGC
ATTTAAAATATATGAGGGTTCTAAAAATTTTTATCCTTGCGTTGAAATAAAGGCTTCT
CCCGCAAAAGTATTACAGGGTCATAATGTTTTTGGTACAACCGATTTAGCTTTATGC
TCTGAGGCTTTATTGCTTAATTTTGCTAATTCTTTGCCTTGCCTGTATGATTTATTGGA
TGTTGGAATTCCTGATGCGGTATTTTCTCCTTACGCATCTGTGCGGTATTTCACACCG
CATATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTTCACCGTC
ATCACCGAAACGCGCGAGACGAAAGGGCCTCGTGATACGCCTATTTTTATAGGTTAA
TGTCATGATAATAATGGTTTCTTAGACGTCAGGTGGCACTTTTCGGGGAAATGTGCG
CGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCA
ACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTG
ACAACGATCGGAGGACCGAAGGAGCTAACCGCTTTTTTGCACAACATGGGGGATCA
TGTAACTCGCCTTGATCGTTGGGAACCGGAGCTGAATGAAGCCATACCAAACGACG
AGCGTGACACCACGATGCCTGTAGCAATGGCAACAACGTTGCGCAAACTATTAACT
GGCGAACTACTTACTCTAGCTTCCCGGCAACAATTAATAGACTGGATGGAGGCGGAT
AAAGTTGCAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGA
TGAACGAAATAGACAGATCGCTGTGAGATAGGTGCCTCACTGATTAAGCATTGGTAAC
TGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGTTAGGCCA
CCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAA
AGCGCCACGCTTCCCGAAGGGAGAAAGGCGGACAGGTATCCGGTAAGCGGCAGGG
TCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCCTCTCC

```
                        -continued
CCGCGCGTTGGCCGATTCATTAATGCAGCAGCTGCGCGCTCGCTCGCTCACTGAGGC
CGCCCGGGCAAAGCCCGGGCGTCGGGCGACCTTTGGTCGCCCGGCCTCAGTGAGCG
AGCGAGCGCGCAGAGAGGGAGTGGCCAACTCCATCACTAGGGGTTCCTTGTAGTTA
ATGATTAACCCGCCATGCTACTTATCTACGTAGCCATGCTCTAGGACATTGATTATTG
ACTAGTGGAGTTCCGCGTTACATAACTTACGGTAAATGGCCCGCCTGGCTGACCGCC
CAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTG
CTTCACTCTCCCCATCTCCCCCCCCTCCCCACCCCCAATTTTGTATTTATTTATTTTTT
AATTATTTTGTGCAGCGATGGGGGCGGGGGGGGGGGGGGCGCGCGCCAGGCGGG
GCGGGGCGGGGCGAGGGGCGGGGGGGGCGAGGCGGAGAGGTGCGGCGGCAGCCA
ATCAGAGCGGCGCGCTCCGAAAGTTTCCTTTTATGGCGAGGCGGCGGCGGCGGCGG
CCCTATAAAAAGCGAAGCGCGCGGCGGGCGGGAGTCGCTGCGCGCTGCCTTCGCCC
CGTGCCCCGCTCCGCCGCCGCCTCGCGCCGCCCGCCCCGGCTCTGACTGACCGCGTT
ACTAAAACAGGTAAGTCCGGCCTCCGCGCCGGGTTTTGGCGCCTCCCGCGGGCGCCC
CCCTCCTCACGGCGAGCGCTGCCACGTCAGACGAAGGGCGCAGCGAGCGTCCTGAT
CCTTCCGCCCGGACGCTCAGGACAGCGGCCCGCTGCTCATAAGACTCGGCCTTAGAA
CCCCAGTATCAGCAGAAGGACATTTTAGGACGGGACTTGGGTGACTCTAGGGCACT
GGTTTTCTTTCCAGAGAGCGGAACAGGCGAGGAAAAGTAGTCCCTTCTCGGCGATTC
TGCGGAGGGATCTCCGTGGGGCGGTGAACGCCGATGATGCCTCTACTAACCATGTTC
ATGTTTTCTTTTTTTTTCTACAGGTCCTGGGTGACGAACAGGGTACCATGGCCACCGG
CTCTCGCACAAGCCTGCTGCTGGCTTTCGGACTGCTGTGCCTGCCTTGGCTCCAGGA
GGGCTCCGCCGCTAGCATCGATACCGTCGCTATGTGCTGGAGGCTTGCTGAAGGCTG
TATGCTGTATCTTCCGGATGTCATAGCGGCGTTTTGGCCTCTGACTGACGCCGCTATG
ATCCGGAAGATACAGGACACAAGGCCTGTTACTAGCACTCACATGGAACAAATGGC
CTCTAGCCTGGAGGCTTGCTGAAGGCTGTATGCTGTATGTTTATGGATCTCACCTGG
CGTTTTGGCCTCTGACTGACGCCAGGTGAGCCATAAACATACAGGACACAAGGCCT
GTTACTAGCACTCACATGGAACAAATGGCCTCTAGCCTGGAGGCTTGCTGAAGGCTG
TATGCTGTCACTTTCAGAAATCATGGGTGCGTTTTGGCCTCTGACTGACGCACCCAT
GATCTGAAAGTGACAGGACACAAGGCCTGTTACTAGCACTCACATGGAACAAATGG
CCTC
3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) with an insert sequence of nucleotides that comprises 95-100% identity to the full length of SEQ ID NO: 2.

2. The composition of claim 1, wherein the insert sequence of nucleotides is encased in a protein coat, a lipid vesicle, or any combination thereof.

3. The composition of claim 1, wherein the insert sequence of nucleotides is encased in a viral vector.

4. The composition of claim 3, wherein the viral vector is one of a double stranded DNA virus, a single stranded DNA virus, a single stranded RNA virus, or a double stranded RNA virus.

5. The composition of claim 3, wherein the viral vector is an adeno-associated virus.

6. A composition that comprises a recombinant plasmid (RP) with a sequence of nucleotides that encodes for a kinase molecule, wherein the sequence comprises 95-100% identity to the full length of SEQ ID NO. 3.

* * * * *

SEQUENCE LISTING

```
Sequence total quantity: 3
SEQ ID NO: 1           moltype = DNA  length = 5807
FEATURE                Location/Qualifiers
source                 1..5807
                       mol_type = other DNA
                       organism = synthetic construct
SEQUENCE: 1
tctagaataa tcaacctctg gattacaaaa tttgtgaaag attgactggt attcttaact   60
atgttgctcc ttttacgcta tgtggatacg ctgctttaat gcctttgtat catgctattg  120
```

```
cttcccgtat ggctttcatt ttctcctcct tgtataaatc ctggttgctg tctctttatg    180
aggagttgtg gcccgttgtc aggcaacgtg gcgtggtgtg cactgtgttt gctgacgcaa    240
cccccactgg ttggggcatt gccaccacct gtcagctcct ttccgggact ttcgctttcc    300
ccctccctat tgccacggcg gaactcatcg ccgcctgcct tgcccgctgc tggacagggg    360
ctcggctgtt gggcactgac aattccgtgg tgttgtcggc gaaatcatcg tccttcctt    420
ggctgctcgc ctgtgttgcc acctggattc tgcgcgggac gtccttctgc tacgtccctt    480
cggccctcaa tccagcggac cttcttcccc cgggcctgct gccggctctg cggcctcttc    540
cgcgtcttcg ccttcgccct cagacgagtc ggatctccct tgggccgcc tccccgccta    600
agcttatcga taccgtcgag atctaacttg tttattgcag cttataatgg ttacaaataa    660
agcaatagca tcacaaattt cacaaataaa gcatttttt cactgcattc tagttgtggt    720
ttgtccaaac tcatcaatgt atcttatcat gtctggatct cgacctcgac tagagcatgg    780
ctacgtagat aagtagcatg gcgggttaat cattaactac aaggaacccc tagtgatgga    840
gttggccact ccctctctgc gcgctcgctc gctcactgag gccgggcgac caaaggtcgc    900
ccgacgcccg ggctttgccc gggcggcctc agtgagcgag cgagcgcgca gctgcgtaa    960
tagcgaagag gcccgcaccg atcgcccttc ccaacagttg cgcagcctga atggcgaatg   1020
gcgattccgt tgcaatggct ggcggtaata ttgttctgga tattaccagc aaggccgata   1080
gtttgagttc ttctactcag gcaagtgatg ttattactaa tcaaagaagt attgcgacaa   1140
cggttaatt gcgtgatgga cagactcttt tactcggtgg cctcactgat tataaaaaca   1200
cttctcagga ttctggcgta ccgttcctgt ctaaaatccc tttaatcggc ctcctgttta   1260
gctcccgctc tgattctaac gaggaaagca cgttatacgt gctcgtcaaa gcaaccatag   1320
tacgcgcct gtagcggcgc attaagcgcg gcgggtgtg tggttacgcg cagcgtgacc   1380
gctacacttg ccagcgccct agcgcccgct ccttcccttc tcttcctcgc ctttctcgcc   1440
acgttcgccg gctttccccg tcaagctcta aatcggggc tccctttagg gttccgattt   1500
agtgctttac ggcacctcga ccccaaaaaa cttgattagg gtgatggttc acgtagtggg   1560
ccatcgccct gatagacggt ttttcgccct tgacgttgg agtccacgtt ctttaatagt   1620
ggactcttgt tccaaactgg aacaacactc aaccctatct cggtctattc ttttgattta   1680
taagggattt tgccgatttc ggcctattgg ttaaaaaatg agctgattta acaaaaattt   1740
aacgcgaatt ttaacaaaat attaacgttt acaatttaaa tatttgctta tacaatcttc   1800
ctgttttgg ggcttttctg attatcaacc ggggtacata tgattgacat gctagtttta   1860
cgattaccgt tcatcgattc tcttgtttgc tccagactct caggcaatga cctgatagcc   1920
tttgtagaga cctctcaaaa atagctaccc tctccggcat gaatttatca gctagaacgt   1980
ttgaatatca tattgatggt gatttgactg tctccggcct ttctcacccg tttgaatctt   2040
tacctacaca ttactcaggc attgcattta aaatatatga gggttctaaa aattttatc   2100
cttgcgttga aataaaggct tctcccgcaa aagtattaca gggtcataat gttttttgta   2160
caaccgattt agctttatgc tctgaggctt tattgcttaa ttttgctaat tctttgcctt   2220
gcctgtatga tttattggat gttggaattc ctgatgcggt attttctcct tacgcatctg   2280
tgcggtattt cacaccgcat atggtgcact ctcagtacaa tctgctctga tgccgcatag   2340
ttaagccagc cccgacaccc gccaacaccc gctgacgcgc cctgacgggc ttgtctgctc   2400
ccggcatccg cttacagaca agctgtgacc gtctccggga gctgcatgtg tcagaggttt   2460
tcaccgtcat caccgaaacg cgcgagacga aagggcctcg tgatacgcct attttttatag   2520
gttaatgtca tgataataat ggtttcttag acgtcaggtg gcacttttcg gggaaatgtg   2580
cgcggaaccc ctatttgttt attttttctaa atacattcaa atatgtatcc gctcatgaga   2640
caataacccct gataaatgct tcaataatat tgaaaaagga agatgag tattcaacat   2700
ttccgtgtcg cccttattcc cttttttgcg gcattttgcc ttcctgtttt tgctcaccca   2760
gaaacgctgg tgaaagtaaa agatgctgaa gatcagttgg gtgcacgagt gggttacatc   2820
gaactggatc tcaacagcgg taagatcctt gagagttttc gccccgaaga acgttttcca   2880
atgatgagca ctttttaaagt tctgctatgt ggcgcggtat tatcccgtat tgacgccggg   2940
caagagcaac tcggtcgccg catacactat tctcagaatg acttggttga gtactcacca   3000
gtcacagaaa agcatcttac ggatggcatg acagtaagag aattatgcag tgctgccata   3060
accatgagtg ataacactgc ggccaactta cttctgacaa cgatcggagg accgaaggag   3120
ctaaccgctt ttttgcacaa catgggggat catgtaactc gccttgatcg ttgggaaccg   3180
gagctgaatg aagccatacc aaacgacgag cgtgacacca cgatgcctgt agcaatggca   3240
acaacgttgc gcaaactatt aactggcgaa ctacttactc tagcttcccg gcaacaatta   3300
atagactgga tggaggcgga taaagttgca ggaccacttc tgcgctcggc ccttccggct   3360
ggctggttta ttgctgataa atctggagcc ggtgagcgtg ggtctcgcgg tatcattgca   3420
gcactgggc cagatggtaa gccctcccgt atcgtagtta tctacacgac ggggagtcag   3480
gcaactatgg atgaacgaaa tagacagatc gctgagatag gtgcctcact gattaagcat   3540
tggtaactgt cagaccaagt ttactcatat atactttaga ttgatttaaa acttcatttt   3600
taattaaaa ggatctaggt gaagatcctt tttgataatc tcatgaccaa aatcccttaa   3660
cgtgagtttt cgttccactg agcgtcagac cccgtagaaa agatcaaagg atcttcttga   3720
gatcctttt ttctgcgcgt aatctgctgc ttgcaaacaa aaaaaccacc gctaccagcg   3780
gtggtttgtt tgccggatca agagctacca actctttttc cgaaggtaac tggcttcagc   3840
agagcgcaga taccaaatac tgtccttcta gtgtagccgt agttaggcca ccacttcaag   3900
aactctgtag caccgcctac atacctcgct ctgctaatcc tgttaccagt ggctgctgcc   3960
agtggcgata agtcgtgtct taccgggttg gactcaagac gatagttacc ggataaggcg   4020
cagcggtcgg gctgaacggg gggttcgtgc acacagccca gcttggagcg aacgacctac   4080
accgaactga gatacctaca gcgtgagcta tgagaaagcg ccacgcttcc gaagggaga   4140
aaggcggaca ggtatccggt aagcggcagg gtcggaacag gagagcgcac gagggagctt   4200
ccagggggaa acgcctggta tctttatagt cctgtcgggt ttcgccacct ctgacttgag   4260
cgtcgatttt tgtgatgctc gtcagggggg cggagcctat ggaaaaacgc cagcaacgcg   4320
gcctttttac ggttcctggc cttttgctgg ccttttgctc acatgttctt tcctgcgtta   4380
tcccctgatt ctgtggataa ccgtattacc gcctttgagt gagctgatac cgctcgccgc   4440
agccgaacga ccgagcgcag cgagtcagtg agcgaggaag cggaagagcg cccaatacgc   4500
aaaccgcctc tccccgcgcg ttggccgatt cattaatgca gctggcacga caggtttccc   4560
tcactgaggc cgcccgggca agcccggcg tcgggcgac ctttggtcgc cggcctcag   4620
tgagcgagc agcgcgcaga gagggagtgg ccaactccat cactagggt tccttgtagt   4680
taatgattaa cccgccatgc tacttatcta cgtagccatg ctctaggaca ttgattattg   4740
actagtggag ttccgcgtta cataacttac ggtaaatggc ccgcctggct gaccgcccaa   4800
cgacccccgc ccattgacgt caataatgac gtatgttccc atagtaacgc caatagggac   4860
```

```
tttccattga cgtcaatggg tggagtattt acggtaaact gcccacttgg cagtacatca   4920
agtgtatcat atgccaagta cgcccccat  tgacgtcaat gacgtaaat  ggcccgcctg   4980
gcattatgcc cagtacatga ccttatggga ctttcctact ggcagtaca  tctacgtatt   5040
agtcatcgct attaccatgg tcgaggtgag ccccacgttc tgcttcactc tccccatctc   5100
ccccccctcc ccaccccccaa ttttgtattt atttattttt taattatttt gtgcagcgat   5160
ggggggcgggg ggggggggggg gcgcgcgcca ggcggggcgg ggcggggcga ggggcggggc  5220
ggggcgaggc ggagaggtgc ggcggcagcc aatcagagcg gcgcgctccg aaagtttcct   5280
tttatggcga ggcggcggcg gcggcggccc tataaaaagc gaagcgcgcg gcgggcggga   5340
gtcgctgcgc gctgccttcg ccccgtgccc cgctccgccg ccgcctcgcg ccgcccgccc   5400
cggctctgac tgaccgcgtt actaaaacag gtaagtccgg cctccgcgcc gggttttggc   5460
gcctcccgcg ggcgccccc  tcctcacggc gagcgctgcc acgtcagacg aagggcgcag   5520
cgagcgtcct gatccttccg cccggacgct caggacagcg gcccgctgct cataagactc   5580
ggccttagaa ccccagtatc agcagaagga cattttagga cgggacttgg gtgactctag   5640
ggcactggtt ttcttttccag agagcggaac aggcgaggaa aagtagtccc ttctcggcga   5700
ttctgcggag ggatctccgt ggggcggtga acgccgatga tgcctctact aaccatgttc   5760
atgttttctt ttttttttcta caggtcctgg gtgacgaaca gggtacc                5807

SEQ ID NO: 2          moltype = DNA   length = 526
FEATURE               Location/Qualifiers
source                1..526
                      mol_type = other DNA
                      organism = synthetic construct
SEQUENCE: 2
atggccaccg gctctcgcac aagcctgctg ctggctttcg gactgctgtg cctgccttgg    60
ctccaggagg gctccgccgc tagcatcgat accgtcgcta tgtgctggag gcttgctgaa   120
ggctgtatgc tgtatcttcc ggatgtcata gcggcgtttg ggcctctgac tgacgcgct   180
atgatccgga agatacagga cacaaggcct gttactagca ctcacatgga acaaatggcc   240
tctagcctgg aggcttgctg aaggctgtat gctgtatgtt tatggatctc acctggcgtt   300
ttggcctctg actgacgcca ggtgagccat aaacatacag gacacaaggc ctgttactag   360
cactcacatg gaacaaatgg cctctagcct ggaggcttgc tgaaggctgt atgctgtcac   420
tttcagaaat catgggtgcg ttttggcctc tgactgacgc acccatgatc tgaaagtgac   480
aggacacaag gcctgttact agcactcaca tggaacaaat ggcctc                  526

SEQ ID NO: 3          moltype = DNA   length = 6333
FEATURE               Location/Qualifiers
source                1..6333
                      mol_type = other DNA
                      organism = synthetic construct
SEQUENCE: 3
tctagaataa tcaacctctg gattacaaaa tttgtgaaag attgactggt attcttaact    60
atgttgctcc ttttacgcta tgtggatacg ctgctttaat gcctttgtat catgctattg   120
cttcccgtat ggctttcatt ttctcctcct tgtataaatc ctggttgctg tctctttatg   180
aggagttgtg gcccgttgtc aggcaacgtg gcgtggtgtg cactgtgttt gctgacgcaa   240
cccccactgg ttggggcatt gccaccacct gtcagctcct ttccgggact ttcgctttcc   300
ccctccctat tgccacggcg gaactcatcg ccgcctgcct tgcccgctgc tggacagggg   360
ctcggctgtt gggcactgac aattccgtgg tgttgtcggg aaatcatcg  tccttttcctt   420
ggctgctcgc ctgtgttgcc acctggattc tgcgcgggac gtccttctgc tacgtccctt   480
cggccctcaa tccagcggac cttccttccc gcggcctgct gccggctctg cggcctcttc   540
cgcgtcttcg ccttcgccct cagacgagtc ggatctccct ttgggccgcc tccccgccta   600
agcttatcga taccgtcgag atctaacttg tttattgcag cttataatgg ttacaaataa   660
agcaatagca tcacaaattt cacaaataaa gcatttttt  cactgcattc tagttgtggt   720
ttgtccaaac tcatcaatgt atcttatcat gtctggatct cgacctcgac tagagcatgc   780
ctacgtagat aagtagcatg gcgggttaat cattaactac aaggaacccc tagtgatgga   840
gttggcact  ccctctctgc gcgctcgctc gctcactgag gccgggcgac caaaggtcgc   900
ccgacgcccg ggctttgccc gggcggcctc agtgagcgag cgagcgcgca gctggcgtaa   960
tagcgaagag gcccgcaccg atcgcccttc ccaacagttg cgcagcctga atggcgaatg   1020
gcgattccgt tgcaatggct ggcggtaata ttgttctgga tattaccagc aaggccgata   1080
gtttgagttc ttctactcag gcaagtgatg ttattactaa tcaaagaagt attgcgacaa   1140
cggttaattt gcgtgatgga cagactcttt tactcggtgg cctcactgat tataaaaaca   1200
cttctcagga ttctggcgta ccgttcctgt ctaaaatccc tttaatcggc ctcctgttta   1260
gctcccgctc tgattctaac gaggaaagca cgttatacgt gctcgtcaaa gcaaccatag   1320
tacgcgccct gtagcggcgc attaagcgcg gcgggtgtgg tggttacgcg cagcgtgacc   1380
gctacacttg ccagcgccct agcgcccgct cctttcgctt tcttcccttc ctttctcgcc   1440
acgttcgccg gctttccccg tcaagctcta aatcggggca tccctttagg gttccgattt   1500
agtgctttac ggcacctcga ccccaaaaaa cttgattagg gtgatggttc acgtagtggt   1560
ccatcgccct gatagacggt ttttcgccct ttgacgttgg agtccacgtt ctttaatagt   1620
ggactcttgt tccaaactgg aacaacactc aaccctatct cggtctattc ttttgattta   1680
taagggattt tgccgatttc ggcctattgg ttaaaaaatg agctgattta acaaaaattt   1740
aacgcgaatt ttaacaaaat attaacgttt acaatttgcc tta tacaatcttc           1800
ctgttttttgg ggcttttctg attatcaacc ggggtacata tgattgacat gctagtttta   1860
cgattaccgt tcatcgattc tcttgtttgc tccagactct caggcaatga cctgatagcc   1920
tttgtagaga cctctcaaaa atagctaccc tctccggcat gaatttatca gctagaacgg   1980
ttgaatatca tattgatggt gatttgactg tctccggcct ttctcacccg tttgaatctt   2040
tacctacaca ttactcaggc attgcattta aaatatatga aggttctaaa aattttttatc   2100
cttgcgttga aataaaggct tctcccgcaa aagtattaca gggtcataat gttttttgta   2160
caaccgattt agctttatgc tctgaggctt tattgcttaa ttttgctaat ctttt gcctt   2220
gcctgtatga tttattggat gttggaattc ctgatgcgtt attttctcct tacgcatctg   2280
tgcggtatt  cacaccgcat atggtgcact ctcagtacaa tctgctctga tgccgcatag   2340
ttaagccagc cccgacaccc gccaacaccc gctgacgcgc cctgacgggc ttgtctgctc   2400
```

```
ccggcatccg cttacagaca agctgtgacc gtctccggga gctgcatgtg tcagaggttt   2460
tcaccgtcat caccgaaacg cgcgagacga aagggcctgc tgatacgcct atttttatag   2520
gttaatgtca tgataataat ggttttcttag acgtcaggtg gcacttttcg gggaaatgtg   2580
cgcggaaccc ctatttgttt attttttctaa atacattcaa atatgtatcc gctcatgaga   2640
caataaccct gataaatgct tcaataatat tgaaaaagga agagtatgag tattcaacat   2700
ttccgtgtcg cccttattcc cttttttgcg gcattttgcc ttcctgtttt tgctcaccca   2760
gaaacgctgg tgaaagtaaa agatgctgaa gatcagttgg gtgcacgagt gggttacatc   2820
gaactggatc tcaacagcgg taagatcctt gagagttttc gccccgaaga acgttttcca   2880
atgatgagca cttttaaagt tctgctatgt ggcgcggtat tatcccgtat tgacgccggg   2940
caagagcaac tcggtcgccg catacactat tctcagaatg acttggttga gtactcacca   3000
gtcacagaaa agcatcttac ggatggcatg acagtaagag aattatgcag tgctgccata   3060
accatgagtg ataacactgc ggccaactta cttctgacaa cgatcggagg accgaaggag   3120
ctaaccgctt ttttgcacaa catgggggat catgtaactc gccttgatcg ttgggaaccg   3180
gagctgaatg aagccatacc aaacgacgag cgtgacacca cgatgcctgt agcaatggca   3240
acaacgttgc gcaaactatt aactggcgaa ctacttactc tagcttcccg gcaacaatta   3300
atagactgga tggaggcgga taaagttgca ggaccacttc tgcgctcggc ccttccggct   3360
ggctggttta ttgctgataa atctggagcc ggtgagcgtg gtctcgcgg tatcattgca   3420
gcactggggc cagatggtaa gccctcccgt atcgtagtta tctacacgac ggggagtcag   3480
gcaactatgg atgaacgaaa tagacagatc gctgagatag gtgcctcact gattaagcat   3540
tggtaactgt cagaccaagt ttactcatat atactttaga ttgatttaaa acttcatttt   3600
taatttaaaa ggatctaggt gaagatcctt tttgataatc tcatgaccaa aatcccttaa   3660
cgtgagtttt cgttccactg agcgtcagac cccgtagaaa agatcaaagg atcttcttga   3720
gatccttttt ttctgcgcgt aatctgctgc ttgcaaacaa aaaaaccacc gctaccagcg   3780
gtggtttgtt tgccggatca agagctacca actctttttc cgaaggtaac tggcttcagc   3840
agagcgcaga taccaaatac tgtccttcta gtgtagccgt agttaggcca ccacttcaag   3900
aactctgtag caccgcctac atacctcgct ctgctaatcc tgttaccagt ggctgctgcc   3960
agtggcgata agtcgtgtct taccgggttg gactcaagac gatagttacc ggataaggcg   4020
cagcggtcgg gctgaacggg gggttcgtgc acacagccca gcttggagcg aacgacctac   4080
accgaactga gatacctaca gcgtgagcta tgagaaagcg ccacgcttcc cgaagggaga   4140
aaggcggaca ggtatccggt aagcggcagg gtcggaacag gagagcgcac gagggagctt   4200
ccagggggaa acgcctggta tctttatagt cctgtcgggt ttcgccacct ctgacttgag   4260
cgtcgatttt tgtgatgctc gtcagggggg cggagcctat ggaaaaacgc cagcaacgcg   4320
gcctttttac ggttcctggc cttttgctgg ccttttgctc acatgttctt tcctgcgtta   4380
tcccctgatt ctgtggataa ccgtattacc gcctttgagt gagctgatac cgctcgccgc   4440
agccgaacga ccgagcgcag cgagtcagtg agcgaggaag cggaagagcg cccaatacgc   4500
aaaccgcctc tccccgcgcg ttggccgatt cattaatgca gcagctgcgc gctcgctcgc   4560
tcactgaggc cgcccgggca aagcccgggc gtcgggcgac ctttggtcgc ccggcctcag   4620
tgagcgagcg agcgcgcaga gagggagtgg ccaactccat cactaggggt tccttgtagt   4680
taatgattaa cccgccatgc tacttatcta cgtagccatg ctctaggaca ttgattattg   4740
actagtggag ttccgcgtta cataacttac ggtaaatggc ccgcctggct gaccgcccaa   4800
cgaccccccgc ccattgacgt caataatgac gtatgttccc atagtaacgc caatagggac   4860
tttccattga cgtcaatggg tggagtattt acggtaaact gcccacttgg cagtacatca   4920
agtgtatcat atgccaagta cgccccctat tgacgtcaat gacggtaaat ggcccgcctg   4980
gcattatgcc cagtacatga cctatgggac ttttcctact tggcagtaca tctacgtatt   5040
agtcatcgct attaccatgg tcgaggtgag ccccacgttc tgcttcactc tccccatctc   5100
cccccccctcc ccaccccaa ttttgtattt atttatttt taattatttt gtgcagcgat   5160
gggggcgggg ggggggggg gcgcgcgcca ggcggggcgg ggcggggcga ggggcggggc   5220
ggggcgaggc ggagaggtgc ggcggcagcc aatcagagcg gcgcgctccg aaagtttcct   5280
tttatgcgca ggcggcggcg gcgcggcccc tataaaaagc gaagcgcgcg gcgggcggga   5340
gtcgctcgcg gctgccttcg ccccgtgccc cgctccgccg ccgcctcgcg ccgcccgccc   5400
cggctctgac tgaccgcgtt actaaaacag gtaagtccgg cctccgcgcc gggttttggc   5460
gcctcccgcg ggcgccccc tcctcacggc gagcgctgcc acgtcagacg aagggcgcag   5520
cgagcgtcct gatccttccg cccggacgct caggacagcg gcccgctgct cataagactc   5580
ggccttagaa ccccagtatc agcagaagga cattttagga cgggacttgg gtgactctag   5640
ggcactggtt ttctttccag agagcggaac aggcgaggaa aagtagtccc ttctcggcga   5700
ttctgcggag ggatccccgt ggggcggtga acgccgatga tgcctctact aaccatgttc   5760
atgttttctt ttttttttcta caggtcctgg gtgacgaaca gggtaccatg ccaccggct   5820
ctcgcacaag cctgctgctg gctttcggac tgctgtgcct gccttggctc cagggggct   5880
ccgccgctag catcgatacc gtcgctatgt gctgaggct tgctgaaggc tgtatgtgt   5940
atcttccgga tgtcatagcg gcgttttggc ctctgactga cgccgctatg atccggaaga   6000
tacaggacac aaggcctgtt actagcactc acatggaaga aatggcctct agcctggagg   6060
cttgctgaag gctgtatgct gtatgtttat ggatctcacc tggcgttttg gcctctgact   6120
gacgccaggt gagccataaa catacaggac acaaggcctg ttactagcac tcacatggaa   6180
caaatggcct ctagcctgga ggcttgctga aggctgtatg ctgtcacttt cagaaatcat   6240
gggtgcgttt tggcctctga ctgacgcacc catgatctga aagtgacagg acacaaggcc   6300
tgttactagc actcacatgg aacaaatggc ctc                                6333
```